United States Patent
Kovatchev et al.

(10) Patent No.: US 10,546,659 B2
(45) Date of Patent: Jan. 28, 2020

(54) METHOD, SYSTEM AND COMPUTER SIMULATION ENVIRONMENT FOR TESTING OF MONITORING AND CONTROL STRATEGIES IN DIABETES

(75) Inventors: Boris P. Kovatchev, Charlottesville, VA (US); Marc D. Breton, Charlottesville, VA (US); Claudio Cobelli, Padua (IT); Chiara Dalla Man, Venice (IT)

(73) Assignee: University of Virginia Patent Foundation, Charlottesville, VA (US)

( * ) Notice: Subject to any disclaimer, the term of this patent is extended or adjusted under 35 U.S.C. 154(b) by 1016 days.

(21) Appl. No.: 12/664,444

(22) PCT Filed: Jun. 20, 2008

(86) PCT No.: PCT/US2008/067725
§ 371 (c)(1),
(2), (4) Date: Dec. 14, 2009

(87) PCT Pub. No.: WO2008/157781
PCT Pub. Date: Dec. 24, 2008

(65) Prior Publication Data
US 2010/0179768 A1    Jul. 15, 2010

Related U.S. Application Data

(60) Provisional application No. 61/073,074, filed on Jun. 17, 2008, provisional application No. 60/936,581, filed on Jun. 21, 2007.

(51) Int. Cl.
*G16H 50/50* (2018.01)
*G16H 20/17* (2018.01)

(52) U.S. Cl.
CPC .............. *G16H 50/50* (2018.01); *G16H 20/17* (2018.01)

(58) Field of Classification Search
None
See application file for complete search history.

(56) References Cited

U.S. PATENT DOCUMENTS 6,835,175 B1 * 12/2004 Porumbescu ................. 600/300
2003/0058245 A1    3/2003 Brazhnik et al.
(Continued)

FOREIGN PATENT DOCUMENTS

WO    02087506 A2    11/2002
WO    03054725 A2    7/2003

OTHER PUBLICATIONS

Mougiakakou et al. (Proceedings of the 2005 IEEE, Engineering in Medicine and Biology 27th Annual Conference, 2005, 298-301).*
(Continued)

*Primary Examiner* — Soren Harward
(74) *Attorney, Agent, or Firm* — Vorys, Sater, Seymour and Pease LLP; Vincent M DeLuca; Robert J. Decker

(57) ABSTRACT

A simulation environment for in silico testing of monitoring methods, open-loop and closed-loop treatment strategies in type 1 diabetes. Some exemplary principal components of the simulation environment comprise, but not limited thereto, the following: 1) a "population" of in silico "subjects" with type 1 diabetes in three age groups; 2) a simulator of CGM sensor errors; 3) a simulator of insulin pumps and discrete insulin delivery; 4) an interface allowing the input of user-specified treatment scenarios; and 5) a set of standardized outcome measures and graphs evaluating the quality of the tested treatment strategies. These components can be used separately or in combination for the preclinical evaluation of open-loop or closed-loop control treatments of diabetes.

20 Claims, 7 Drawing Sheets

(56) References Cited

U.S. PATENT DOCUMENTS

| | | | | |
|---|---|---|---|---|
| 2004/0133455 A1* | 7/2004 | McMahon | ......... | G06F 19/3418 |
| | | | | 705/3 |
| 2005/0131663 A1* | 6/2005 | Bangs | .................... | G16H 50/50 |
| | | | | 703/11 |
| 2005/0272640 A1* | 12/2005 | Doyle, III | .............. | A61B 5/411 |
| | | | | 435/14 |
| 2005/0288910 A1 | 12/2005 | Schlessinger et al. | | |
| 2006/0272652 A1* | 12/2006 | Stocker | ................. | G16H 50/50 |
| | | | | 128/898 |
| 2007/0026365 A1* | 2/2007 | Friedrich | ............. | G06F 19/324 |
| | | | | 434/127 |
| 2007/0038475 A1* | 2/2007 | Schlessinger et al. | .......... | 705/2 |

OTHER PUBLICATIONS

Fone et al. (Systematic review of the use and value of computer simulation modeling in the population health and healthcare delivery, Journal of Public Heath Medicine, 2003, vol. 25, No. 4, p. 325-335; see specifically abstract; p. 325-326, p. 332, left column, penultimate paragraph).*

Chase, J. G. et al. Model-based glycaemic control in critical care—A review of the state of the possible. Biomedical Signal Processing and Control 1, 3-21 (2006).*

Chassin, L. J., Wilinska, M. E. & Hovorka, R. Evaluation of glucose controllers in virtual environment: Methodology and sample application. Artificial Intelligence in Medicine 32, 171-181 (2004).*

The extended European Search Report dated Jul. 5, 2013.

* cited by examiner

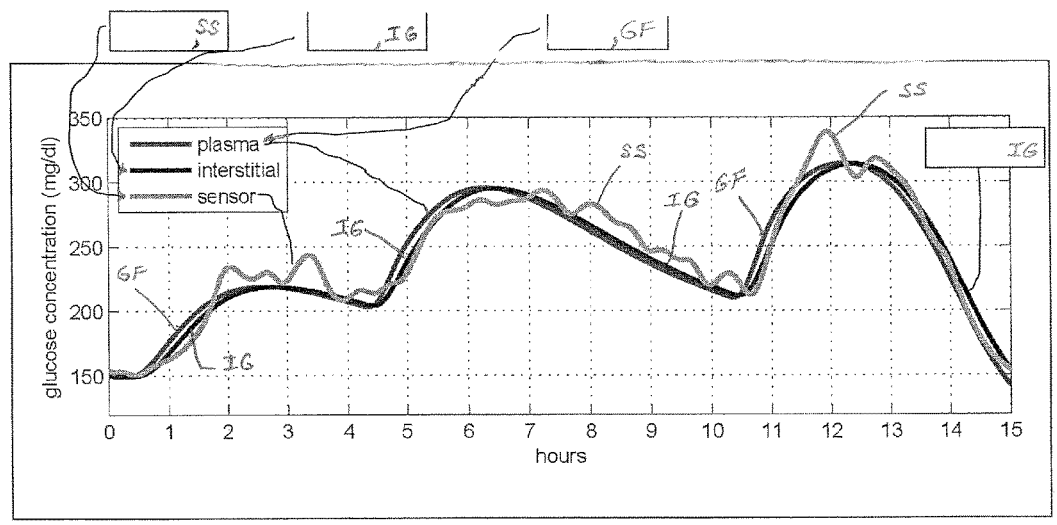
FIG. 4
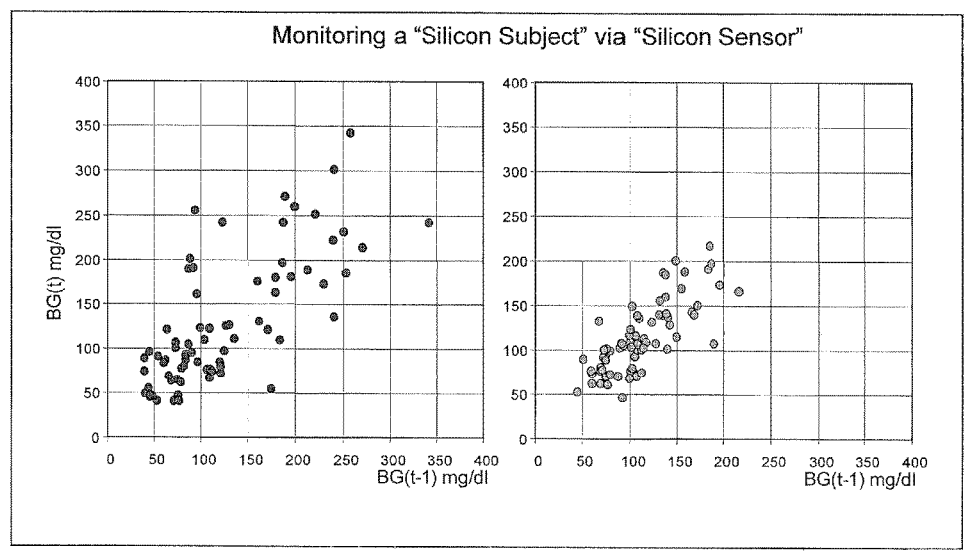
FIG. 5A  FIG. 5B

METHOD, SYSTEM AND COMPUTER SIMULATION ENVIRONMENT FOR TESTING OF MONITORING AND CONTROL STRATEGIES IN DIABETES

RELATED APPLICATIONS

The present application is a national stage filing of International Application No. PCT/US2008/067725, filed Jun. 20, 2008, which claims priority under 35 U.S.C. § 119(e) from U.S. Provisional Application Ser. No. 60/936,581, filed Jun. 21, 2007, entitled "Computer Simulation Environment in Silico Testing of Continuous Glucose Monitoring and Optimal Metabolic Control in Diabetes;" and U.S. Provisional Application Ser. No. 61/073,074, filed Jun. 17, 2008, entitled "Computer Simulation Environment in Silico Testing of Continuous Glucose Monitoring and Optimal Metabolic Control in Diabetes;" the disclosures of which are hereby incorporated by reference herein in their entirety.

BACKGROUND OF THE INVENTION

Thirty years ago, the possibility for external closed-loop control of blood glucose (BG) levels in people with diabetes has been established with an instrument commercially known as the Biostator™, which used intravenous (i.v.) BG sampling and i.v. insulin and glucose delivery [1],[2],[3]. Recent studies of i.v. closed-loop control performed at the University of Virginia by Dr. Clarke (who has also been involved in the first Biostator™ studies) showed that i.v. control algorithms are capable of keeping BG levels within 10% from the preset targets during maintained euglycemia, descent into induced hypoglycemia, sustained hypoglycemia (at 50 mg/dl for 30 minutes), and controlled recovery [4]. However, i.v. closed-loop control is cumbersome and unsuited for outpatient use. Thus, increasing academic, industrial, and political effort has been focused on the development of minimally-invasive closed loop using subcutaneous (s.c.) systems using continuous glucose monitoring (CGM) and s.c. insulin delivery. Several s.c.-s.c. systems, generally using CGM coupled with insulin infusion pump and a control algorithm, have been tested [5],[6],[7],[8]. A recent United States Senate hearing emphasized the artificial pancreas initiative [9]. In September 2006 the Juvenile Diabetes Research Foundation (JDRF) initiated the Artificial Pancreas Project and funded six centers worldwide to carry closed-loop glucose control research [10]. These centers include the universities of Cambridge (England), Colorado, Santa Barbara, Stanford, Virginia, and Yale. So far, preliminary results have been reported from three closed-loop control studies conducted at Medtronic [8], Cambridge [6], and Yale using equipment provided by Medtronic MiniMed Inc.

The future development of the artificial pancreas will be greatly accelerated by employing mathematical modeling and computer simulation. Such in silico testing would provide direction for clinical studies, out-ruling ineffective control scenarios in a cost-effective manner. In the past two decades computer simulation and computer-aided design have made dramatic progress in all areas of design of complex engineering systems. A prime example is the Boeing 777 jetliner, which has been recognized as the first airplane to be 100% digitally designed and assembled in computer simulation environment. This virtual design has eliminated the need for many costly experiments and accelerated the development process. The final result has been impressive—the 777's flight deck and passenger cabin received the Design Excellence Award of the Industrial Designers Society—the first time any airplane was recognized by the society [11]. In the area of diabetes, accurate prediction of clinical trials has been done by the Archimedes diabetes model [12], [13]; a company—Entelos, Inc.—specializes in predictive biosimulation and in particular is working on diabetes simulator. These existing diabetes simulators, however, are based on population models. As a result, their capabilities are limited to prediction of population averages that would be observed during clinical trials.

The ability to simulate glucose-insulin system in normal life condition can be very useful in diabetes research. Several simulation models have been proposed in literature which proved to be useful in tackling various aspects of pathophysiology of diabetes [32-42]. Recently a new meal simulation model was proposed in [43]. The novelty and strength of this model is that it is based on virtually model-independent measurements of the various glucose and insulin fluxes occurring during a meal [44, 45]. In fact, the system is very complex and only the availability of glucose and insulin fluxes, in addition to their plasma concentrations, has allowed us to minimize structural uncertainties in modeling the various processes. The model may comprise of 12 nonlinear differential equations, 18 algebraic equations and 35 parameters. A user-friendly simulation software of this model would be of great help especially for investigators without a specific expertise in modeling. An aspect of the present invention is to present the interactive software GIM (Glucose Insulin Model), implemented in MATLAB version 7.0.1 which allows to simulate both normal and pathological conditions, e.g. type 2 diabetes and open- and closed-loop insulin infusion in type 1 diabetes. These case studies are only presented to illustrate the potential of the software and do not aim to address pathophysiological questions or to assess quality of glucose control by different strategies Therefore, for the purposes of artificial pancreas development, a different type of computer simulator is needed—a system that is capable of simulating the glucose-insulin dynamics of a particular person.

SUMMARY OF THE INVENTION

An aspect of an embodiment of the present invention provides a simulation environment for in silico testing of monitoring methods, open-loop and closed-loop treatment strategies in Type 1 diabetes. Some exemplary principal components of the simulation environment comprise, but not limited thereto, the following: 1) a "population" of 300 in silico "subjects" (as population as desired or required) with type 1 diabetes in three age groups (or other age groups as desired or required); 2) a simulator of CGM sensor errors; 3) a simulator of insulin pumps and discrete insulin delivery; 4) an interface allowing the input of user-specified treatment scenarios; and 5) a set of standardized outcome measures and graphs evaluating the quality of the tested treatment strategies. These components can be used separately or in combination for the preclinical evaluation of open-loop or closed-loop control treatments of diabetes.

Further, the present invention technology has been approved by the Food and Drug Administration (FDA) as a substitute for animal trials in testing of control algorithms for type 1 diabetes, which obviates the need for certain pre-clinical safety trials in animals.

An aspect of an embodiment of the present invention provides a computer implemented method for testing of monitoring and/or treatment strategies for diabetes using a computer simulation environment. The testing method comprises representation of the human metabolic system. The representation of the human metabolic system may include: applying a mathematical model of the human metabolic system; and providing a plurality of instances of a simulated subject, creating a simulated population.

The population may be a representative of the general diabetic population or other desired demographic. The plurality of instances may a variety of desired or required levels, including less than about 100, about 100, about 200, about 300, and/or greater than 300. The testing method may comprise a representation of the errors of continuous glucose monitoring sensor. The testing method may comprise a representation of subcutaneous insulin delivery via insulin pump. The method may comprise providing an interactive module for allowing a user or device to interact with the testing method or module to implement the method or system accordingly.

An aspect of an embodiment of the present invention provides a computer simulation system environment for testing of monitoring and/or treatment strategies for diabetes. The computer simulation system environment may comprise: a representation module of the human metabolic system. The representation module comprises a processor configured to: apply a mathematical model means of the human metabolic system, and provide a plurality of instances of simulated subjects comprising a simulated population. The population may be a representative of the general diabetic population or other desired demographic. The plurality of instances may be less than about 100, about 100, about 200, about 300 and/or greater than 300, or as desired or required. The computer simulation system environment for testing may comprise: a simulated monitoring sensor, whereby the simulated monitoring sensor comprises a representation of the errors of continuous glucose monitoring sensor. The computer simulation system environment for testing may comprise a simulated insulin pump, whereby the simulated insulin pump comprises a representation of subcutaneous insulin delivery via insulin pump. The system may comprise an interactive module, whereby the interactive module may be for allowing a user or device to interact with the computer simulation system environment for testing so as to implement the testing.

An aspect of an embodiment of the present invention provides a computer program product comprising a computer useable medium having computer program logic for enabling at least one processor in a computer system for testing of monitoring and/or treatment strategies for diabetes using a computer simulation environment. The testing method via the computer program logic may comprise a representation of the human metabolic system. The representation of the human metabolic system may comprise: applying a mathematical model of the human metabolic system; and providing a plurality of instances of a simulated subject, creating a simulated population.

The invention itself, together with further objects and attendant advantages, will best be understood by reference to the following detailed description taken in conjunction with the accompanying drawings.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which:

FIG. 4 graphically illustrates the errors of a simulated "sensor" which monitors the glucose fluctuations GF of a "subject" simulated by the GIM.

FIGS. 5(A)-(B) graphically present Poincaré plot of glucose dynamics of a person with Type 1 diabetes pre-islet transplantation and post islet-transplantation, respectively.

DETAILED DESCRIPTION OF THE INVENTION

Principal Components of Computer Simulation Environment

Figure 1:
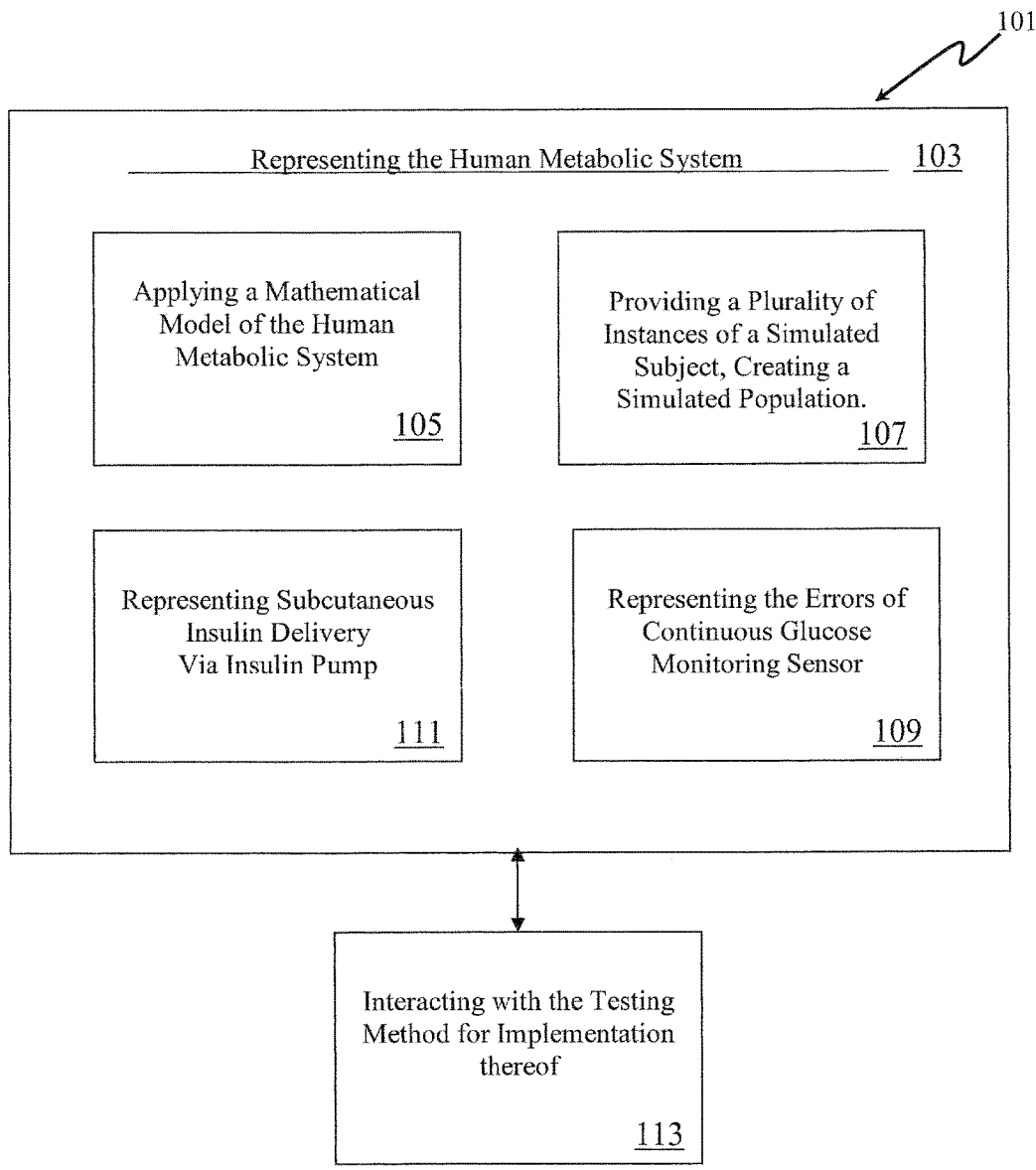
FIG. 1 provides
Figure 2:
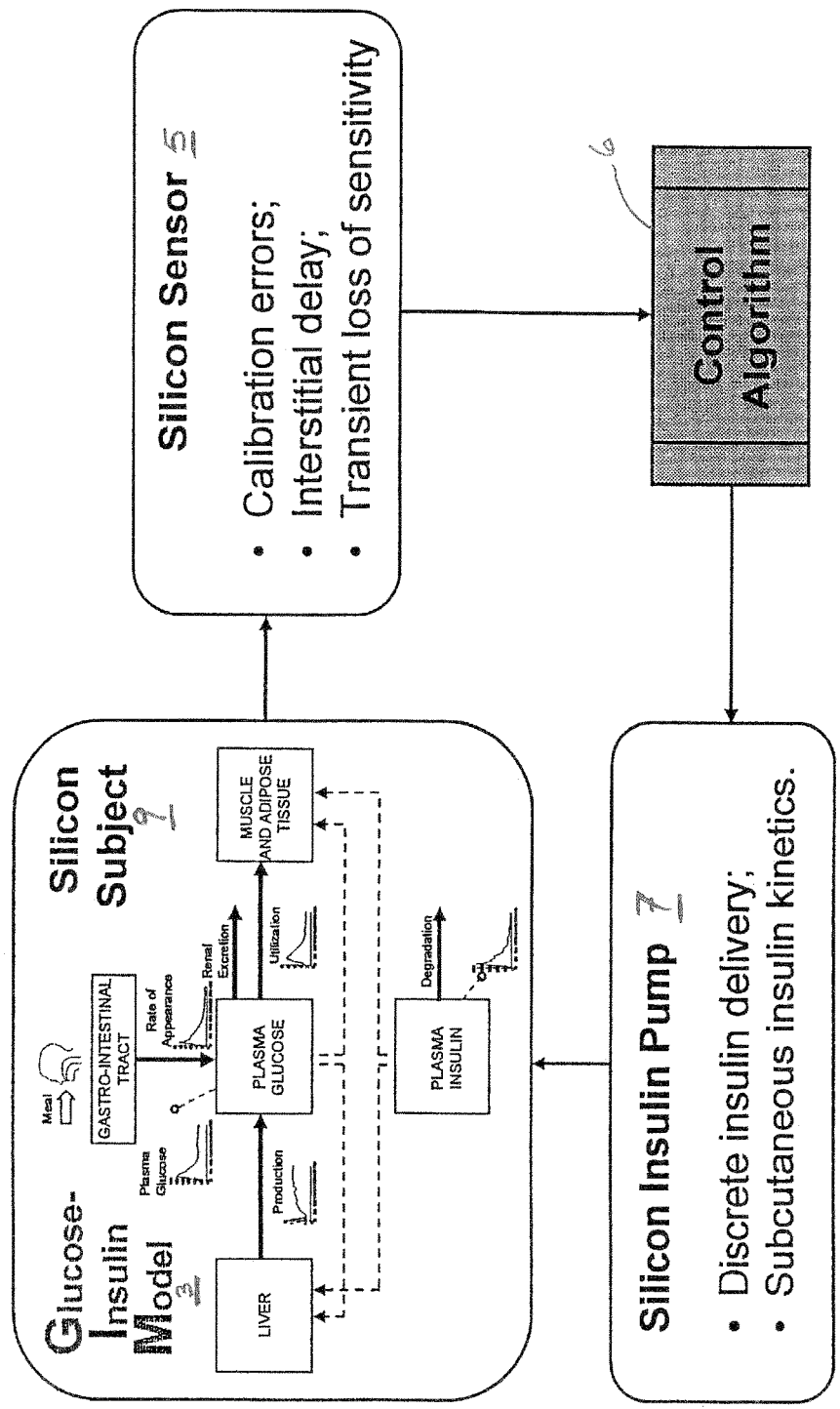
FIG. 2 provides a schematic block diagram of the components of the computer simulation environment.

In an embodiment, a computer simulation environment (i.e., testing platform) for a system using s.c. CGM and s.c. insulin delivery via insulin pump would be a feasible step to validation of treatment strategies in type 1 diabetes (T1DM). Such a computer simulation environment (i.e., testing platform) may have three principal components: the simulated continuous monitoring sensor 5 providing frequent interstitial glucose determinations, the simulated insulin pump 7 delivering subcutaneous insulin and the simulated metabolic system of the person. In an embodiment the computer simulation environment (i.e., testing platform) may be comprised of the following three components as shown in FIG. 2:

a. The Meal Simulator Glucose-Insulin Model (GIM) 3, currently implemented in Simulink® or may be other simulation and Model-Based Design or software, and equipped with individual parameters for 300 subjects with T1DM, or any number as desired or required;

b. The simulator of sensor errors 5, and c. The model of an insulin pump 7 ensuring discrete insulin delivery.

An aspect of the present invention method, system and computer program product provides means for testing of monitoring and/or treatment strategies for diabetes using a computer simulation environment, 101. The means for testing of the monitoring and/or treatment strategies includes representing the Human Metabolic System, 103. The representation module includes: applying a Mathematical Model of the Human Metabolic System, 105 and Providing a Plurality of Instances of a Simulated Subject, Creating a Simulated Population, 107. The means for testing includes representing of the Errors Of Continuous Glucose Monitoring Sensor, 109. The means for testing includes representing of Subcutaneous Insulin Delivery Via Insulin Pump, 111. Moreover, an interactive module is provided for allowing a user or device to interact with the testing means 113, accordingly as desired and required and as discussed throughout this disclosure.

"Silicon Subject 9"—the Glucose-Insulin Model of the Human Metabolic System

Dr. Claudio Cobelli pioneered, together with Richard Bergman, the mathematical modeling of glucose metabolism. Their, now classic, Minimal Model of Glucose Kinetics [14] served as the basis for numerous further developments (generating over 600 publications in the last 30 years), and as a gold-standard assessment of insulin sensitivity (Si) in humans. Dr. Cobelli's group has been at the forefront of these investigations, with more than 200 publications addressing aspects of glucose-insulin dynamics. Recently their studies have been extended to measure the same indices in the postprandial condition [15],[16],[17]. The minimal model and its generalizations allow therefore the estimation, for each individual, of his/her parameters of insulin sensitivity and insulin action.

Referring to an aspect of the present invention, the metabolic system of a particular person can be programmed into a computer simulator creating a "silicon subject 9" whose metabolism is closely related to its human original. In silico refers to, for example but not limited thereto, in computer simulation or in virtual reality.

A new generation of in silico model has very recently become possible thanks to a database collected by a study at the Division of Endocrinology, Diabetes, Metabolism & Nutrition, Mayo Clinic, Rochester, Minn., directed by Dr. Robert A. Rizza. A unique meal data set of 204 nondiabetic individuals with various degrees of glucose tolerance has become available. The subjects underwent a triple tracer meal protocol, thus allowing us to obtain in a virtually model-independent fashion the time course of all the relevant glucose and insulin fluxes during a meal i.e. glucose rate of appearance in plasma, production, utilization and pancreatic insulin secretion [18],[19]. Thus, by using a "concentration and flux," it was possible to model the glucose-insulin system by resorting to a sub-system forcing function strategy, which minimizes structural uncertainties in modeling the various unit processes.

In order to simulate the metabolic system of a person with T1DM, the in silico model has been modified. First, the insulin secretion module has been eliminated. Then, in the model of glucose production the control of portal insulin has been removed due to the absence of insulin secretion. Glucose production was assumed to be higher on average (relative to non-diabetic subjects), e.g. 2.4 mg/kg/min. Finally, some steady state constrains have been altered to accommodate these model modifications.

Figure 3A:
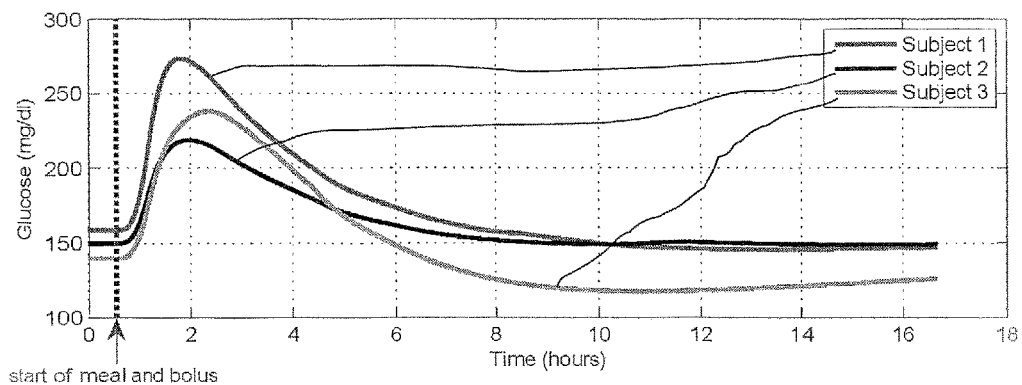
FIG. 3(A) graphically presents the glycemic reaction of three simulated "subjects" 9 after a meal and pre-meal insulin bolus, FIG. 3(B) graphically presents the reaction of one simulated "subject" 9 to three meals with different carbohydrate content: 75, 85, and 95 grams.
Figure 3B:
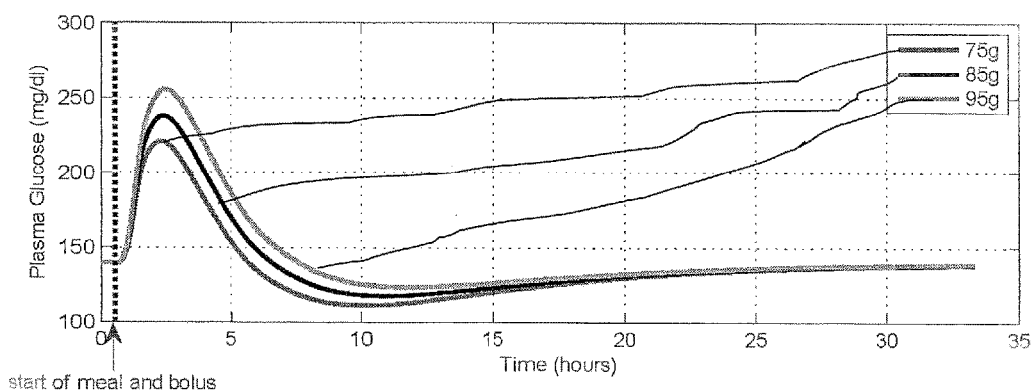

An important aspect to realistic computer simulation is the availability of "silicon subjects 9," e.g. the availability of distributions of the model parameters across the population. Such distributions are difficult to obtain and are considered the "secret" allowing successful simulation. The identification of the simulation model in the database described above has provided estimates of all model parameters. This allowed the computer simulation of various metabolic scenarios on a "cohort" of "silicon subjects." For example, FIG. 3(A) graphically presents the glycemic reaction of three "simulated or silicon subjects 9" after a meal and pre-meal insulin bolus, while FIG. 3(B) graphically presents the reaction of one "subject" 9 to three meals with different carbohydrate content: 75, 85, and 95 grams. The current software implementation of the T1DM model is equipped with 300 "silicon subjects," which will allow the development of unified approach to the testing of closed-loop control algorithms 6.

The model glucose-insulin system or the glucose-insulin model (GIM) 3 puts in relation the measured plasma concentrations of glucose (G) and insulin (I) and the glucose fluxes (i.e. rate of appearance, Ra, endogenous glucose production, EGP, utilization, U, renal extraction, E, and insulin fluxes, i.e. secretion, S, and degradation D) in a person with Type 1 diabetes.

In particular, glucose kinetics is described by the two compartment model:

$$\begin{cases} \dot{G}_p(t) = EGP(t) + Ra(t) - U_{ii}(t) - E(t) - k_1 \cdot G_p(t) + k_2 \cdot G_t(t) & G_p(0) = G_{pb} \\ \dot{G}_t(t) = -U_{id}(t) + k_1 \cdot G_p(t) - k_2 \cdot G_t(t) & G_t(0) = G_{tb} \\ G(t) = \dfrac{G_p}{V_G} & G(0) = G_b \end{cases}$$

where $G_p$ and $G_t$ (mg/kg) are glucose masses in plasma and rapidly-equilibrating tissues, and in slowly-equilibrating tissues, respectively, G (mg/dl) plasma glucose concentration, suffix b denotes basal state, EGP endogenous glucose production (mg/kg/min), Ra glucose rate of appearance in plasma (mg/kg/min), E renal excretion (mg/kg/min), $U_{ii}$ and $U_{id}$ insulin-independent and dependent glucose utilizations, respectively (mg/kg/min), $V_G$ distribution volume of glucose (dl/kg), and $k_1$ and $k_2$ (min$^{-1}$) rate parameters.

At basal steady state the endogenous production $EGP_b$ equals glucose disappearance, i.e. the sum of glucose utilization and renal excretion (which is zero in health), $U_b+E_b$.

The functional description of EGP in terms of glucose and insulin signals comprises a direct glucose signal and both delayed and anticipated insulin signals:

$$EGP(t)=k_{p1}-k_{p2} \cdot G_p(t)-k_{p3} \cdot I_d(t)-k_{p4} \cdot I_{po}(t)$$
$$EGP(0)=EGP_b$$

where $I_{po}$ is the amount of insulin in the portal vein (pmol/kg), $I_d$(pmol/l) is a delayed insulin signal realized with a chain of two compartments:

$$\begin{cases} \dot{I}_1(t) = -k_i \cdot [I_1(t) - I(t)] & I_1(0) = I_b \\ \dot{I}_d(t) = -k_i \cdot [I_d(t) - I_1(t)] & I_d(0) = I_b \end{cases}$$

$k_{p1}$ (mg/kg/min) is the extrapolated EGP at zero glucose and insulin, $k_{p2}$ (min$^{-1}$) liver glucose effectiveness, $k_{p3}$ (mg/kg/min per pmol/l) parameter governing amplitude of insulin action on the liver, $k_{p4}$ (mg/kg/min/(pmol/kg)) parameter governing amplitude of portal insulin action on the liver and $k_i$ (min$^{-1}$) rate parameter accounting for delay between insulin signal and insulin action. EGP is also constrained to be non-negative.

At basal steady state one has:

$$k_{p1}=EGP_b+k_{p2} \cdot G_{pb}+k_{p3} \cdot I_b+k_{p4} \cdot I_{pob}$$

The model of glucose intestinal absorption describes the glucose transit through the stomach and intestine by assuming the stomach to be represented by two compartments (one for solid and one for triturated phase), while a single compartment is used to describe the gut:

$$\begin{cases} Q_{sto}(t) = Q_{sto1}(t) + Q_{sto2}(t) & Q_{sto}(0) = 0 \\ \dot{Q}_{sto1}(t) = -k_{gri} \cdot Q_{sto1}(t) + D \cdot \delta(t) & Q_{sto1}(0) = 0 \\ \dot{Q}_{sto2}(t) = -k_{empt}(Q_{sto}) \cdot Q_{sto2}(t) + k_{gri} \cdot Q_{sto1}(t) & Q_{sto2}(0) = 0 \\ \dot{Q}_{gut} = -k_{abs} \cdot Q_{gut}(t) + k_{empt}(Q_{sto}) \cdot Q_{sto2}(t) & Q_{gut}(0) = 0 \\ Ra(t) = \dfrac{f \cdot k_{abs} \cdot Q_{gut}(t)}{BW} & Ra(0) = 0 \end{cases}$$

where $Q_{sto}$ (mg) is amount of glucose in the stomach (solid, $Q_{sto1}$, and liquid phase, $Q_{sto2}$), $Q_{gut}$ (mg) glucose mass in the intestine, $k_{gri}$ (min$^{-1}$) rate of grinding, $k_{empt}(Q_{sto})$ (min$^{-1}$) rate constant of gastric emptying which is a nonlinear function of $Q_{sto}$:

$$k_{empt}(Q_{sto}) = k_{min} + \frac{k_{max} - k_{min}}{2} \cdot \left\{ \begin{array}{l} \tanh[\alpha(Q_{sto} - b \cdot D)] - \\ \tanh[\beta(Q_{sto} - c \cdot D)] + 2 \end{array} \right\}$$

and $k_{abs}$ (min$^{-1}$) rate constant of intestinal absorption, f fraction of intestinal absorption which actually appears in plasma, D (mg) amount of ingested glucose, BW (kg) body weight and Ra (mg/kg/min) appearance rate of glucose in plasma.

The model of glucose utilization by body tissues during a meal (both insulin-independent and -dependent) assumes that glucose utilization is made up of two components. Insulin-independent utilization takes place in the first compartment, is constant and represents glucose uptake by the brain and erythrocytes ($F_{cns}$):

$$U_{ii}(t) = F_{cns}$$

Insulin-dependent utilization takes place in the remote compartment and depends nonlinearly (Michaelis Menten) from glucose in the tissues:

$$U_{id}(t) = \frac{[V_{mo} + V_{mx} \cdot X(t)] \cdot G_t(t)}{K_{m0} + G_t(t)}$$

where remote insulin, X(t), is given by:

$$\dot{X}(t) = -p_{2U} \cdot X(t) + p_{2U}[I(t) - I_b]$$
$$X(0) = 0$$

where I is plasma insulin, suffix b denotes basal state, $p_{2U}$ (min$^{-1}$) is rate constant of insulin action on the peripheral glucose utilization.

Total glucose utilization, U, is thus:

$$U(t) = U_{ii}(t) + U_{id}(t)$$

At basal steady state one has:

$$G_{tb} = \frac{F_{cns} - EGP_b + k_1 \cdot G_{pb}}{k_2}$$

and:

$$U_b = EGP_b = F_{cns} + \frac{V_{m0} \cdot G_{tb}}{K_{m0} + G_{tb}}$$

from which:

$$V_{m0} = \frac{(EGP_b - F_{cns}) \cdot (K_{m0} + G_{tb})}{G_{tb}}.$$

Glucose excretion by the kidney occurs if plasma glucose exceeds a certain threshold and can be modeled by a linear relationship with plasma glucose:

$$E(t) = \begin{cases} k_{e1} \cdot [G_p(t) - k_{e2}] & \text{if } G_p(t) > k_{e2} \\ 0 & \text{if } G_p(t) \leq k_{e2} \end{cases}$$

where $k_{e1}$ (min$^{-1}$) is glomerular filtration rate and $k_{e2}$ (mg/kg) renal threshold of glucose.

Population of Simulated "Subjects"

As noted above, the key to successful simulation is the availability of comprehensive population of simulated "subjects" that encompasses the distribution of key metabolic parameters observed in Type 1 diabetes in vivo. Next, the Biometric data (age, weight, insulin units per day, carbohydrate ratio, and maximal glucose decrease) for the population of 300 in silico subjects 9 are as follows: 100 adults, 100 adolescents, and 100 children. Carbohydrate ratio is computed from total daily insulin using standard 450 rule. The maximal glucose decrease (MGD) is computed as the maximum decrease in glucose following a simulated administration of one unit insulin.

TABLE 1

| ADULTS | | | | | ADOLESCENTS | | | | | CHILDREN | | | | | |
|---|---|---|---|---|---|---|---|---|---|---|---|---|---|---|---|
| ID | Age [y] | Weight [kg] | Total daily insulin [U] | CHO ratio [g/U] | MGD [mg/dl] | ID | Age [y] | Weight [kg] | Total daily insulin [U] | CHO ratio [g/U] | MGD [mg/dl] | ID | Age [y] | Weight [kg] | Total daily insulin [U] | CHO ratio [g/U] | MGD [mg/dl] |
| 51 | 24 | 76.4 | 38.9 | 11.6 | 13.2 | 31 | 16 | 54.3 | 51.6 | 8.7 | 10.5 | 11 | 11 | 58.9 | 26.0 | 17.3 | 32.9 |
| 52 | 27 | 102.6 | 34.3 | 13.1 | 31.0 | 32 | 15 | 60.8 | 59.5 | 7.6 | 10.5 | 12 | 7 | 24.8 | 21.9 | 20.5 | 73.8 |
| 53 | 70 | 74.6 | 61.4 | 7.3 | 3.0 | 33 | 13 | 44.7 | 37.3 | 12.1 | 23.8 | 13 | 10 | 46.9 | 16.6 | 27.0 | 45.2 |
| 54 | 62 | 57.3 | 28.7 | 15.7 | 59.9 | 34 | 16 | 60.4 | 38.8 | 11.6 | 9.8 | 14 | 10 | 51.6 | 46.8 | 9.6 | 20.4 |
| 55 | 40 | 59.1 | 40.6 | 11.1 | 15.1 | 35 | 12 | 45.3 | 37.3 | 12.1 | 21.4 | 15 | 7 | 43.5 | 18.7 | 24.1 | 74.4 |
| 56 | 77 | 68.7 | 43.0 | 10.5 | 19.0 | 36 | 16 | 50.6 | 50.8 | 8.9 | 8.0 | 16 | 7 | 38.2 | 45.3 | 9.9 | 13.8 |
| 57 | 23 | 67.3 | 27.5 | 16.4 | 22.0 | 37 | 15 | 46.0 | 63.3 | 7.1 | 7.8 | 17 | 9 | 34.6 | 48.4 | 9.3 | 42.8 |
| 58 | 47 | 68.3 | 33.5 | 13.4 | 37.4 | 38 | 12 | 51.2 | 53.2 | 8.5 | 5.6 | 18 | 7 | 38.2 | 32.3 | 13.9 | 58.9 |
| 59 | 44 | 64.0 | 52.1 | 8.6 | 17.6 | 39 | 12 | 50.8 | 57.2 | 7.9 | 5.7 | 19 | 10 | 36.8 | 59.8 | 7.5 | 13.9 |
| 60 | 66 | 66.6 | 41.2 | 10.9 | 17.0 | 40 | 15 | 48.8 | 70.7 | 6.4 | 5.7 | 20 | 11 | 58.1 | 45.8 | 9.8 | 30.2 |

Provided below is a reference list of the description of 26 in silico parameters defining each silicon subject 9.

$k_{abs}$=rate constant of glucose absorption by the intestine
$k_{max}$=maximum rate constant of gastric emptying
$k_{min}$=minimum rate constant of gastric emptying
b=percentage of the dose for which $k_{empt}$ decreases at $(k_{max}-k_{min})/2$
d=percentage of the dose for which $k_{empt}$ is back to $(k_{max}-k_{min})/2$
$k_i$=rate parameter accounting for delay between insulin signal and insulin action on the liver
$k_{p2}$=liver glucose effectiveness
$k_{p3}$=parameter governing amplitude of insulin action on the liver
$V_g$=distribution volume of glucose
$V_{mx}$=parameter governing amplitude of insulin action on glucose utilization
$k_{m0}$=parameter governing glucose control on glucose utilization
$K_2$=rate parameter accounting for glucose transit from tissue to plasma
$p_{2U}$=rate parameter accounting for delay between insulin signal and insulin action on glucose utilization
$V_i$=distribution volume of insulin
$m_1$=rate parameter of insulin kinetics
$m_5$=coefficient linking insulin hepatic extraction to insulin secretion rate
$G_b$=basal glucose concentration
$EGP_b$=basal endogenous glucose production
BW=body weight
$I_b$=basal insulin concentration (resulting from a basal insulin infusion rate)
CL=insulin clearance
$k_d$=rate constant of nonmonomeric insulin dissociation
$k_{sc}$=rate constant taking into account the physiological delay of the sensor
$k_{a1}$=rate constants of nonmonomeric insulin absorption
$k_{a2}$=rate constants of monomeric insulin absorption Provided below in tables 2 and 3, is a sample list of In Silico Model Parameters for 10 Test adults.

TABLE 2

| ID numbers 51-60, Parameters kabs to K1 | | | | | | | | | | | | |
| --- | --- | --- | --- | --- | --- | --- | --- | --- | --- | --- | --- | --- |
| ID | kabs | kmax | kmin | b | d | ki | kp2 | kp3 | Vg | Vmx | km0 | K2 | K1 |
| 51 | 0.111 | 0.031 | 0.006 | 0.812 | 0.129 | 0.006 | 0.004 | 0.008 | 1.748 | 0.030 | 199.5 | 0.098 | 0.053 |
| 52 | 0.195 | 0.028 | 0.008 | 0.802 | 0.191 | 0.007 | 0.002 | 0.022 | 1.703 | 0.029 | 215.2 | 0.067 | 0.078 |
| 53 | 0.510 | 0.023 | 0.016 | 0.943 | 0.119 | 0.006 | 0.010 | 0.003 | 1.836 | 0.027 | 238.1 | 0.344 | 0.045 |
| 54 | 0.759 | 0.025 | 0.009 | 0.944 | 0.188 | 0.007 | 0.002 | 0.016 | 1.753 | 0.096 | 217.7 | 0.116 | 0.079 |
| 55 | 0.036 | 0.051 | 0.011 | 0.657 | 0.124 | 0.004 | 0.006 | 0.007 | 1.830 | 0.049 | 240.5 | 0.109 | 0.061 |
| 56 | 0.154 | 0.027 | 0.006 | 0.893 | 0.249 | 0.003 | 0.002 | 0.012 | 1.677 | 0.043 | 228.1 | 0.189 | 0.086 |
| 57 | 0.026 | 0.065 | 0.007 | 0.622 | 0.139 | 0.011 | 0.010 | 0.006 | 1.566 | 0.059 | 220.5 | 0.060 | 0.076 |
| 58 | 0.928 | 0.019 | 0.009 | 0.875 | 0.216 | 0.005 | 0.005 | 0.021 | 1.717 | 0.069 | 227.1 | 0.037 | 0.071 |
| 59 | 0.097 | 0.031 | 0.007 | 0.853 | 0.115 | 0.010 | 0.011 | 0.006 | 1.837 | 0.061 | 226.9 | 0.116 | 0.072 |
| 60 | 0.983 | 0.019 | 0.014 | 0.776 | 0.228 | 0.010 | 0.003 | 0.005 | 2.016 | 0.048 | 246.6 | 0.127 | 0.066 |

TABLE 3

| Adults: ID numbers 51-60, Parameters p2U to ka2 | | | | | | | | | | | | |
| --- | --- | --- | --- | --- | --- | --- | --- | --- | --- | --- | --- | --- |
| ID | p2U | Vi | m1 | m5 | Gb | EGPb | BW | Ib | CL | kd | ksc | ka1 | ka2 |
| 51 | 0.015 | 0.059 | 0.156 | 0.043 | 151.3 | 3.001 | 76.37 | 90.56 | 1.033 | 0.017 | 0.108 | 0.001 | 0.007 |
| 52 | 0.030 | 0.062 | 0.326 | 0.083 | 157.5 | 2.351 | 102.62 | 88.51 | 1.098 | 0.017 | 0.091 | 0.002 | 0.016 |
| 53 | 0.012 | 0.049 | 0.104 | 0.021 | 152.3 | 2.864 | 74.61 | 69.24 | 1.005 | 0.017 | 0.071 | 0.001 | 0.012 |
| 54 | 0.047 | 0.060 | 0.186 | 0.041 | 154.4 | 2.475 | 57.32 | 103.75 | 0.925 | 0.016 | 0.045 | 0.002 | 0.012 |
| 55 | 0.033 | 0.043 | 0.085 | 0.030 | 139.7 | 2.953 | 59.06 | 93.76 | 1.162 | 0.015 | 0.065 | 0.002 | 0.020 |
| 56 | 0.013 | 0.058 | 0.205 | 0.029 | 154.9 | 2.602 | 68.71 | 96.16 | 1.224 | 0.016 | 0.128 | 0.002 | 0.014 |
| 57 | 0.027 | 0.075 | 0.550 | 0.030 | 128.4 | 2.616 | 67.32 | 70.25 | 1.160 | 0.019 | 0.176 | 0.001 | 0.014 |
| 58 | 0.034 | 0.063 | 0.190 | 0.042 | 149.5 | 2.872 | 68.28 | 94.61 | 1.145 | 0.013 | 0.129 | 0.001 | 0.012 |
| 59 | 0.017 | 0.107 | 0.172 | 0.024 | 145.3 | 3.132 | 64.00 | 138.98 | 1.136 | 0.017 | 0.112 | 0.002 | 0.016 |
| 60 | 0.018 | 0.070 | 0.135 | 0.017 | 140.8 | 3.415 | 66.63 | 81.65 | 1.141 | 0.014 | 0.108 | 0.002 | 0.026 |

$K_1$=rate parameter accounting for glucose transit from plasma to tissue

Provided below in tables 4 and 5, is a sample list of In Silico Model Parameters for 10 Test adolescents.

TABLE 4

| ID numbers 31-40, Parameters kabs to K1 | | | | | | | | | | | | |
| --- | --- | --- | --- | --- | --- | --- | --- | --- | --- | --- | --- | --- |
| ID | kabs | kmax | kmin | b | d | ki | kp2 | kp3 | Vg | Vmx | km0 | K2 | K1 |
| 31 | 0.101 | 0.050 | 0.009 | 0.623 | 0.116 | 0.004 | 0.012 | 0.004 | 1.860 | 0.030 | 231.3 | 0.047 | 0.086 |
| 32 | 0.140 | 0.040 | 0.008 | 0.824 | 0.118 | 0.003 | 0.004 | 0.002 | 1.793 | 0.020 | 214.3 | 0.084 | 0.072 |
| 33 | 0.209 | 0.042 | 0.019 | 0.786 | 0.056 | 0.004 | 0.008 | 0.003 | 1.964 | 0.052 | 187.0 | 0.056 | 0.075 |
| 34 | 0.194 | 0.028 | 0.009 | 0.698 | 0.237 | 0.004 | 0.005 | 0.007 | 1.819 | 0.018 | 218.2 | 0.054 | 0.058 |
| 35 | 0.235 | 0.036 | 0.007 | 0.739 | 0.168 | 0.006 | 0.004 | 0.009 | 1.979 | 0.037 | 228.5 | 0.069 | 0.064 |
| 36 | 0.021 | 0.092 | 0.007 | 0.664 | 0.091 | 0.007 | 0.004 | 0.004 | 1.830 | 0.020 | 244.6 | 0.093 | 0.052 |

TABLE 4-continued

ID numbers 31-40, Parameters kabs to K1

| ID | kabs | kmax | kmin | b | d | ki | kp2 | kp3 | Vg | Vmx | km0 | K2 | K1 |
|---|---|---|---|---|---|---|---|---|---|---|---|---|---|
| 37 | 1.555 | 0.022 | 0.015 | 1.011 | 0.170 | 0.003 | 0.005 | 0.003 | 2.057 | 0.022 | 239.7 | 0.074 | 0.079 |
| 38 | 0.079 | 0.037 | 0.010 | 0.615 | 0.122 | 0.007 | 0.012 | 0.002 | 1.710 | 0.022 | 242.3 | 0.124 | 0.068 |
| 39 | 1.730 | 0.016 | 0.003 | 0.766 | 0.371 | 0.003 | 0.006 | 0.019 | 1.892 | 0.012 | 307.4 | 0.117 | 0.058 |
| 40 | 0.142 | 0.047 | 0.019 | 0.699 | 0.187 | 0.003 | 0.012 | 0.004 | 1.685 | 0.018 | 269.7 | 0.103 | 0.090 |

TABLE 5

Adolescents: ID numbers 31-50, Parameters p2U to ka2

| ID | p2U | Vi | m1 | m5 | Gb | EGPb | BW | Ib | CL | kd | ksc | ka1 | ka2 |
|---|---|---|---|---|---|---|---|---|---|---|---|---|---|
| 31 | 0.033 | 0.034 | 0.241 | 0.021 | 129.5 | 2.732 | 54.33 | 118.71 | 1.229 | 0.016 | 0.117 | 0.002 | 0.022 |
| 32 | 0.022 | 0.028 | 0.073 | 0.015 | 135.8 | 2.208 | 60.75 | 99.83 | 1.064 | 0.015 | 0.058 | 0.002 | 0.019 |
| 33 | 0.031 | 0.042 | 0.230 | 0.033 | 135.7 | 2.712 | 44.71 | 102.53 | 1.123 | 0.015 | 0.104 | 0.002 | 0.031 |
| 34 | 0.027 | 0.031 | 0.133 | 0.006 | 144.9 | 2.810 | 60.44 | 78.68 | 0.976 | 0.017 | 0.119 | 0.001 | 0.011 |
| 35 | 0.032 | 0.056 | 0.325 | 0.041 | 143.2 | 2.896 | 45.26 | 97.62 | 1.056 | 0.019 | 0.082 | 0.002 | 0.018 |
| 36 | 0.014 | 0.037 | 0.076 | 0.012 | 152.5 | 3.070 | 50.60 | 72.21 | 1.165 | 0.014 | 0.069 | 0.003 | 0.027 |
| 37 | 0.014 | 0.048 | 0.203 | 0.025 | 124.4 | 2.735 | 46.01 | 133.78 | 1.200 | 0.016 | 0.068 | 0.003 | 0.021 |
| 38 | 0.014 | 0.055 | 0.076 | 0.031 | 126.9 | 2.994 | 51.16 | 93.13 | 1.058 | 0.018 | 0.056 | 0.004 | 0.046 |
| 39 | 0.016 | 0.042 | 0.104 | 0.022 | 161.0 | 2.792 | 50.75 | 116.57 | 1.206 | 0.016 | 0.104 | 0.002 | 0.029 |
| 40 | 0.025 | 0.050 | 0.117 | 0.019 | 135.6 | 3.342 | 48.83 | 146.65 | 1.212 | 0.018 | 0.064 | 0.003 | 0.030 |

Provided below in tables 6 and 7, is a sample list of In Silico Model Parameters for 10 Test Children.

TABLE 6

ID numbers 11-20, Parameters kabs to K1

| ID | kabs | kmax | kmin | b | d | ki | kp2 | kp3 | Vg | Vmx | km0 | K2 | K1 |
|---|---|---|---|---|---|---|---|---|---|---|---|---|---|
| 11 | 0.794 | 0.027 | 0.005 | 0.771 | 0.136 | 0.020 | 0.005 | 0.013 | 1.932 | 0.082 | 244.0 | 0.223 | 0.069 |
| 12 | 0.455 | 0.039 | 0.023 | 0.591 | 0.186 | 0.013 | 0.013 | 0.036 | 2.020 | 0.182 | 210.9 | 0.042 | 0.072 |
| 13 | 0.126 | 0.040 | 0.011 | 0.710 | 0.145 | 0.044 | 0.011 | 0.018 | 1.904 | 0.141 | 202.1 | 0.161 | 0.056 |
| 14 | 0.628 | 0.018 | 0.011 | 0.882 | 0.141 | 0.018 | 0.011 | 0.014 | 1.844 | 0.114 | 249.8 | 0.210 | 0.067 |
| 15 | 0.432 | 0.045 | 0.010 | 0.899 | 0.183 | 0.007 | 0.002 | 0.037 | 1.835 | 0.100 | 230.6 | 0.057 | 0.115 |
| 16 | 0.248 | 0.048 | 0.003 | 0.699 | 0.221 | 0.010 | 0.003 | 0.009 | 1.838 | 0.067 | 268.8 | 0.214 | 0.036 |
| 17 | 0.029 | 0.093 | 0.013 | 0.664 | 0.065 | 0.020 | 0.018 | 0.037 | 1.657 | 0.160 | 313.7 | 0.200 | 0.128 |
| 18 | 0.051 | 0.038 | 0.010 | 0.691 | 0.183 | 0.028 | 0.003 | 0.011 | 1.737 | 0.163 | 238.3 | 0.189 | 0.062 |
| 19 | 0.028 | 0.064 | 0.006 | 0.656 | 0.194 | 0.023 | 0.004 | 0.012 | 1.687 | 0.070 | 271.6 | 0.374 | 0.052 |
| 20 | 0.026 | 0.067 | 0.002 | 0.702 | 0.185 | 0.012 | 0.004 | 0.027 | 2.106 | 0.075 | 219.3 | 0.074 | 0.041 |

TABLE 7

Children: ID numbers 11-20, Parameters p2U to ka2

| ID | p2U | Vi | m1 | m5 | Gb | EGPb | BW | Ib | CL | kd | ksc | ka1 | ka2 |
|---|---|---|---|---|---|---|---|---|---|---|---|---|---|
| 11 | 0.052 | 0.054 | 0.080 | 0.034 | 146.9 | 3.263 | 58.86 | 79.79 | 0.903 | 0.016 | 0.058 | 0.003 | 0.023 |
| 12 | 0.089 | 0.034 | 0.242 | 0.022 | 132.9 | 3.198 | 24.76 | 89.90 | 0.920 | 0.014 | 0.119 | 0.002 | 0.027 |
| 13 | 0.059 | 0.069 | 0.302 | 0.090 | 139.6 | 3.288 | 46.85 | 62.27 | 0.838 | 0.014 | 0.107 | 0.002 | 0.020 |
| 14 | 0.082 | 0.036 | 0.080 | 0.018 | 147.2 | 2.845 | 51.60 | 127.54 | 1.188 | 0.014 | 0.045 | 0.001 | 0.011 |
| 15 | 0.083 | 0.080 | 0.831 | 0.016 | 139.8 | 2.812 | 43.47 | 71.72 | 0.891 | 0.017 | 0.091 | 0.001 | 0.010 |
| 16 | 0.074 | 0.047 | 0.242 | 0.013 | 146.3 | 2.647 | 38.19 | 103.26 | 1.218 | 0.015 | 0.075 | 0.003 | 0.022 |
| 17 | 0.088 | 0.032 | 0.159 | 0.012 | 132.7 | 4.101 | 34.59 | 163.74 | 1.121 | 0.017 | 0.178 | 0.003 | 0.043 |
| 18 | 0.056 | 0.030 | 0.068 | 0.005 | 144.7 | 2.720 | 38.24 | 99.97 | 0.978 | 0.015 | 0.136 | 0.003 | 0.034 |
| 19 | 0.048 | 0.033 | 0.137 | 0.007 | 139.3 | 2.908 | 36.82 | 129.32 | 1.442 | 0.017 | 0.045 | 0.001 | 0.014 |
| 20 | 0.080 | 0.038 | 0.278 | 0.018 | 140.4 | 2.863 | 58.06 | 106.42 | 1.465 | 0.014 | 0.100 | 0.003 | 0.029 |

"Silicon Sensor 5"

Dr. Kovatchev's group has been involved in studies of CGM since the introduction of this technology. Many of these studies focused on accuracy of continuous monitoring sensors and on analysis of their errors. For example, in 2004 we introduced the Continuous Glucose Error-Grid Analysis (CG-EGA, [20]), which is still the only method for assessment of the dynamical accuracy of CGM. The CG-EGA has been designed with closed-loop control in mind—it assesses the accuracy of the clinical decisions taken on the basis of sensor data at short (e.g. 10-minute) time intervals. This initial development was followed by extensive studies of sensor accuracy, which allowed not only comparison of various sensors [21], but also the decomposition of sensor errors into errors due to calibration and errors dues to blood-to-interstitial glucose transfer [22]. These methods provide the base for realistic simulation of the errors that a CGM can make and include the resulting noise in the feed for the control algorithm 6, effectively creating a "silicon sensor."

Referring to FIG. 4, FIG. 4 graphically presents the main steps of adding a silicon sensor, which monitors the glucose fluctuations GF of a "silicon subject" simulated by the GIM. The "silicon sensor" SS is vulnerable to interstitial glucose IG delays, calibration and random errors. FIG. 4 graphically provides information on monitoring a "silicon subject" via "silicon sensor".

It is worth noting that sensor errors are typically not random and are poorly represented by white noise. Thus, standard techniques based on adding independent identically distributed Gaussian noise to the output of the GIM simulation would not produce realistic sensor scenarios. Characteristics, such as degree of dependence between sequential readings, influence of calibration errors, and potential for loss of sensitivity need to be taken into account. We also acknowledge that in addition to common sensor error patterns, there exist device-specific errors. Thus, the "silicon sensor" needs to have the capability of representing most popular continuous monitoring devices. Such a capability would allow investigating the performance of control algorithms 6 with various sensors, and potentially optimal pairing between a sensor and a control algorithm 6. Currently, most extensively developed is the silicon image of the FreeStyle Navigator® (Abbott Diabetes Care). However, recently completed accuracy studies would provide data for the simulating of Guardian® RT (Medtronic Inc.) and DexCom™ STS® (Dexcom, Inc.) sensors.

In summary, regarding an aspect of the present invention the addition of "silicon sensor" 5 allows for testing control algorithms 6 under realistic "noisy" conditions. Initial experiments show that such an approach is very beneficial, sometimes suggesting significant changes and rethinking of control strategies.

Regarding an aspect of an embodiment of the present invention, extensive analysis of sensor errors resulted in the following model equations defining in silico continuous glucose sensor (CGS) 5. The errors of the following devices can be simulated by this model: Guardian$^{RT}$ (Medtronic, Northridge, Calif.); Freestyle Navigator™ (Abbott Diabetes Care, Alameda, Calif.); and DexCom™ STS™ (DexCom, Inc. San Diego, Calif.) 7-day sensor. It may be noted that the simulator is not suitable for modeling the errors of the DexCom™ 3-day sensor.

The sensor model was initially derived via analysis of a large data set collected using the Freestyle Navigator™ (Abbott Diabetes Care, Alameda, Calif.). Further NIH-sponsored study at the University of Virginia found that the errors of Guardian$^{RT}$ (Medtronic, Northridge, Calif.) have similar structure and can be modeled by the simulator. Recently, we analyzed accuracy data for the DexCom™ STS™ 7-day sensor (DexCom, Inc. San Diego, Calif.) provided by Decom Inc, and found that this sensor is compatible with the simulation procedure as well. Analysis of DexCom™ STS™ 3-day sensor found that the errors of this device have larger magnitude and therefore could not be simulated in this environment. The errors of these three differ from random noise by having substantial time-lag dependence and other non-i.i.d. characteristics. The components of sensor error were therefore modeled as:

(i) Blood-to-interstitium glucose transport described by the equation:

$$\frac{\partial IG}{\partial t} = -\frac{1}{\tau}(IG - BG)$$

Here IG is the interstitial and BG is plasma glucose concentration; τ represents the time lag between the two fluids.
(ii) Sensor lag—the time of glucose transport from interstitium to the sensor needle:

$$\frac{\partial G}{\partial t} = -\frac{1}{\tau_N}(G - IG)$$

Considering that these are two sequential first order diffusion models, we model them with one diffusion equation where the time lag is the resultant single diffusion process representing both the physiological lag and the sensor lag. Empirical estimation gives a time lag of 5 min (which produces a delay of approximately 15 minutes).

(iii) The noise of the sensor is non-white (Gaussian).

$$\begin{cases} e_1 = v_1 \\ e_n = 0.7 * (e_{n-1} + v_n) \end{cases}$$

$$v_n \sim \Phi(0, 1) \ iid$$

$$\varepsilon_n = \xi + \lambda \sinh\left(\frac{e_n - \gamma}{\delta}\right)$$

An approach of an aspect of the present invention uses Autoregressive Moving Average (ARMA) process for its modeling. The sensor noise is $\varepsilon_n$, which is driven by the normally distributed time series $e_n$. The parameters ξ, λ, δ, and γ are the Johnson system (SU—unbounded system) parameters corresponding to the empirical noise distributions.

Figure 6:
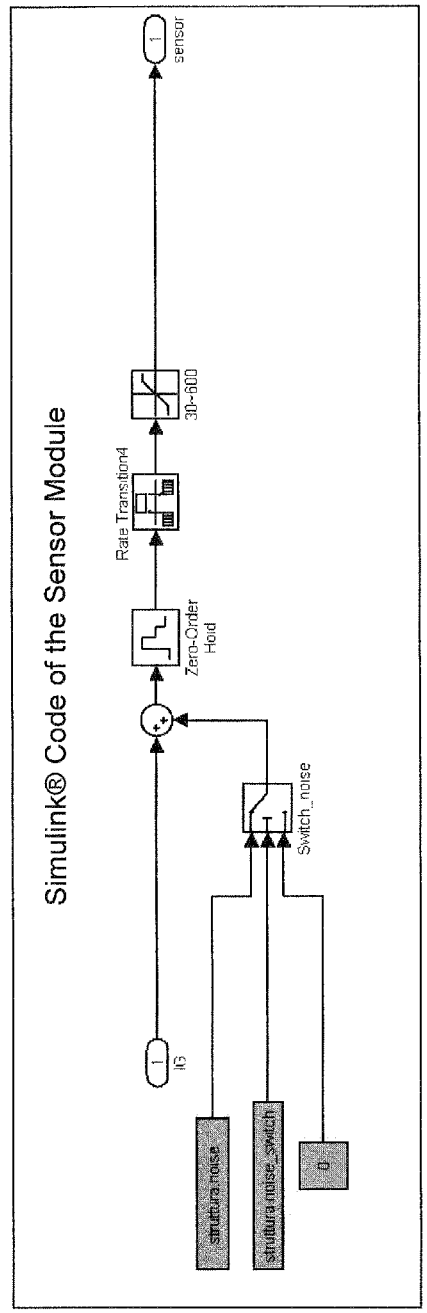
FIG. 6 provides a schematic block diagram of the Simulink model silicon sensor module.

The sensor model was initially derived via analysis of a large data set collected using the Freestyle Navigator™ (Abbott Diabetes Care, Alameda, Calif.). Further, we analyzed accuracy data for two other sensors: Guardian$^{RT}$ (Medtronic, Northridge, Calif.) and DexCom™ STS™-3-Day sensor (DexCom, Inc. San Diego, Calif.), collected during NIH-sponsored study at the University of Virginia. This study showed that the distribution and the range of the errors of the Navigator™ and the Guardian$^{RT}$ were generally equivalent, which allowed the errors of these two devices to be simulated by the same in silico routine. However, this study also showed that the errors of the DexCom™ STS™-3-Day sensor were approximately 30% larger, which prevented this device from inclusion in the simulation environment. The simulink model 43 of the sensor is provided in FIG. 6. The input (IG) is added to the sensor noise coming from struttura.noise. The switch_noise block allows for testing with a simulated perfect sensor: by setting the struttura.noise_switch to a number greater than 0 struttura.noise is replaced by constant1 (i.e. 0). The zero order hold enables discrete sampling at rate equal to struttura.sensor_sampling, and the '30-600' saturation block enforces the hardwired limitation of the sensor (struttura.sensor_min and max). The noise is generated off-line prior to the simulation run as a vector of values with a 1 minute resolution. The create_noise.m script generates the noise vector and loads it into the Matlab workspace, from where it is accessible to the simulator.

"Silicon Insulin Pump"

Subcutaneous insulin delivery via insulin pump has two major specifics that need to be taken into account when testing control algorithms 6 in silico: (i) time and dynamics of insulin transport from subcutaneous compartment into blood, and (ii) discrete insulin infusion corresponding to stepwise basal pump rate and insulin boluses.

A subcutaneous insulin infusion module has been added to the model to account for the exogenous route of insulin delivery in T1DM. Several models of subcutaneous insulin kinetics have been published [23]. The model implemented by Dr. Cobelli assumes a two compartment description for insulin in the subcutaneous space: the first compartment represents the amount of the nonmonomeric insulin, which is then transformed into monomeric insulin (second compartment):

$$\begin{cases} \dot{I}_l(t) = -(m_1 + m_3) \cdot I_l(t) + m_2 \cdot I_p(t) & I_l(0) = I_{lb} \\ \dot{I}_p(t) = -(m_2 + m_4) \cdot I_p(t) + m_1 \cdot I_l(t) + \text{Pump}(t) & I_p(0) = I_{pb} \\ I(t) = \frac{I_p}{V_I} & I(0) = I_b \end{cases}$$

where $I_p$ and $I_l$ (pmol/kg) are insulin masses in plasma and in liver, respectively, I (pmol/l) plasma insulin concentration, suffix b denotes basal state, Pump is the external insulin pump, $m_1$, $m_2$, $m_3$, $m_4$ (min$^{-1}$) rate parameters; $m_3$ depends on basal hepatic extraction, $HE_b$:

$$m_3 = \frac{HE_b \cdot m_1}{1 - HE_b}$$

Discrete insulin delivery is implemented in a pump-specific manner, currently simulation the functioning of Deltec Cozmo® insulin pump, Smiths Medical MD, Inc.

As with "silicon sensors," regarding an aspect of the present invention the parameters of various insulin pumps will be implemented into the simulation environment, which will create an array of insulin delivery options available to the control algorithms 6.

An aspect of the present invention models the subcutaneous insulin pump 7 as a discrete amount, continuous time, insulin delivery device. To reproduce as closely as possible real life pumps, we constraint possible injections, following manufacturers characteristics.

Figure 7:
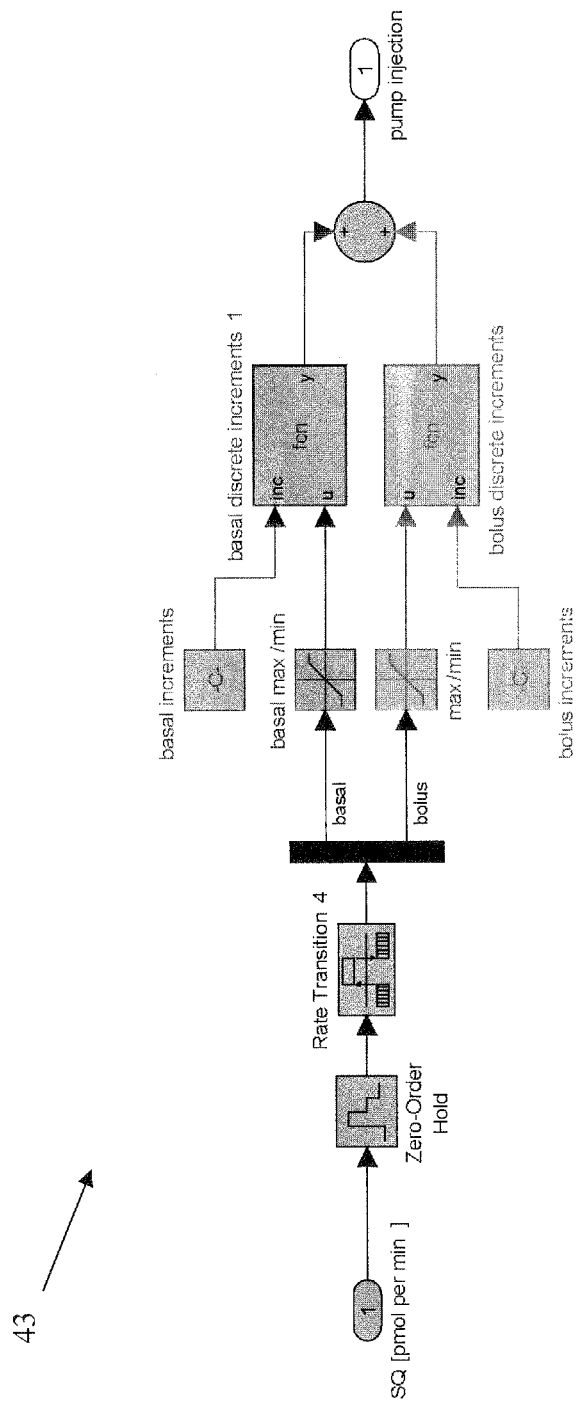
FIG. 7 provides a schematic block diagram of the Simulink model of the subcutaneous insulin pump.

The simulink model 43 of the pump is provided in FIG. 7. The input signal (SQ on the graph) is composed of 2 components: a basal rate and a bolus, therefore representing the two possible modes of classical SQ insulin pumps. Each component is controlled by a different set of rules (e.g. minimum and maximum injection) and these rules are enforced differentially (blue and pink blocks in FIG. 7). Finally both regulated signals are combined to provide the final insulin injection rate. This is implemented as follows:

$$J_R = inc \times div(J_2, inc)$$

$$J_2 = \begin{cases} J & \text{if } \min < J < \max \\ \min & \text{if } J \leq \min \\ \max & \text{if } J \geq \max \end{cases}$$

where JR is the regulated signal (basal or bolus), and min, max and inc are the rule parameters (different for boluses and basal). div( ) is the integer division operator (div(7,3)=2).

These model equations are suitable for in silico simulation of the following insulin pumps:

Deltec Cozmo® (Smiths Medical MD, Inc., St. Paul, Minn.), with parameters:
  Basal Increments 0.05 units/hour; Minimum Bolus Increment 0.05 units;
  Minimum basal rate 0 units/hour; Minimum Bolus Amount 0 units;
  Maximum Basal Rate 35 units/hour; Maximum Bolus Amount 75 units.

OmniPod Insulin Management System (Insulet Corporation, Bedford, Mass.) with parameters:
  Basal Increments 0.05 units/hour; Minimum Bolus Increment 0.05 units;
  Minimum basal rate 0 units/hour; Minimum Bolus Amount 0 units;
  Maximum Basal Rate 30 units/hour; Maximum Bolus Amount 30 units.

While the maximum bolus amounts of these two devices differ, the critical characteristics of the in silico pump model—basal and bolus increments—are identical. Because the simulation of closed-loop control uses basal and bolus increments proposed by the control algorithm 6 and is not dependent on maximal basal/bolus amounts (as long as they are sufficiently large as is the case with these two pumps), we concluded that the Deltec Cozmo® and the OmniPod can be simulated by essentially the same simulation module, with a minor difference in allowable maximum bolus amount and basal rate.

Outcome Measures

To facilitate the interpretation of the results from various control strategies and to permit their direct comparison, a set of indices of glucose control will be implemented within the simulation environment. Emphasis will be placed on indices of temporal glucose variability and associated risks for hypoglycemia and hyperglycemia. This choice is directed by the basic premise of the artificial pancreas—beta cell replacement. In health, the beta cell reacts to temporal glucose fluctuations and aims the maintenance of equilibrium with minimum glucose excursion and particular attention to hypoglycemia, which is controlled by elaborate counterregulatory mechanisms. Average glycemia and clinically accepted standards, such as time spent within a preset target range, will be used as well. The suggested here criteria for testing the performance of control algorithms 6, as well as a set of figures visualizing the results have been previously published and shown to be quite sensitive to the effects of various treatments [24],[25]. In particular, we would suggest temporal glucose variability plots including traces of risks for hypoglycemia and hyperglycemia, as well as Poincaré plot of glucose dynamics. The latter is particularly representative of system stability—the principal property that should be achieved via closed loop control.

Referring to FIG. 5, FIG. 5 graphically presents Poincaré plot of glucose dynamics of a person with Type 1 diabetes pre-islet transplantation (FIG. 5(A)), post islet-transplantation (FIG. 5(B)). Although post-transplantation this person has not been insulin-independent, it is evident that the transplantation has restored partially the stability of this person's glucose-insulin system.

Suggested composite numerical measures of algorithm performance include average glucose for the duration of the experiment, as well as the following indices:

(a) Low Blood Glucose Index (LBGI,), which captures the propensity of the algorithm to overshoot the target and eventually trigger hypoglycemia;

(b) High Blood glucose index (HBGI), which captures the propensity of the algorithm to stay above the target range and even more to "bounce out" of the target range due to oscillations;

(c) Percent of time spent within a preset target range (e.g. 70-180 mg/dl);

(d) Average Absolute Rate of Change, which captures the smoothness of the control algorithm—the more aggressive an algorithm and the less robust to noise in the signal, the bigger the absolute rate of change;

(e) Numerical measures of system stability, such as the diameter of a Poincaré plot.

An embodiment of the present invention simulation environment may be modular, with "plug-and-play" capabilities for algorithm implementation, as well as for adding new silicon "subjects," "sensors," and insulin delivery systems. Unified software platform and outcome measures will allow the widespread implementation this simulation environment.

Further, the unified computer simulation environment should be accepted as a standard testing platform and as a prerequisite for insulin treatment strategy performance (i.e. a treatment needs to be able to control the simulator first, before attempting to control a person).

A simulation model of the glucose-insulin system in normal life condition can be very useful in diabetes research, e.g. testing insulin infusion algorithms and decision support systems, assessing glucose sensor performance, patient and student training An aspect of the present invention method, system and computer program product provides a new meal simulation model, which incorporates state of art quantitative knowledge on glucose metabolism and its control by insulin both at the organ/tissue and whole-body level. An aim of an embodiment of the present invention is to present the interactive simulation software, GIM (Glucose Insulin Model), which implements this model.

For instance, the model (and related method, system and computer program product) may be implemented in MAT-LAB, or any other software platform or program, and may be designed with a windows interface (or other operating system interface or communication) which allows the user to easily simulate 24 hours daily life (or other time period as desired or required) of a type 1 diabetic subject.

Figure 8:
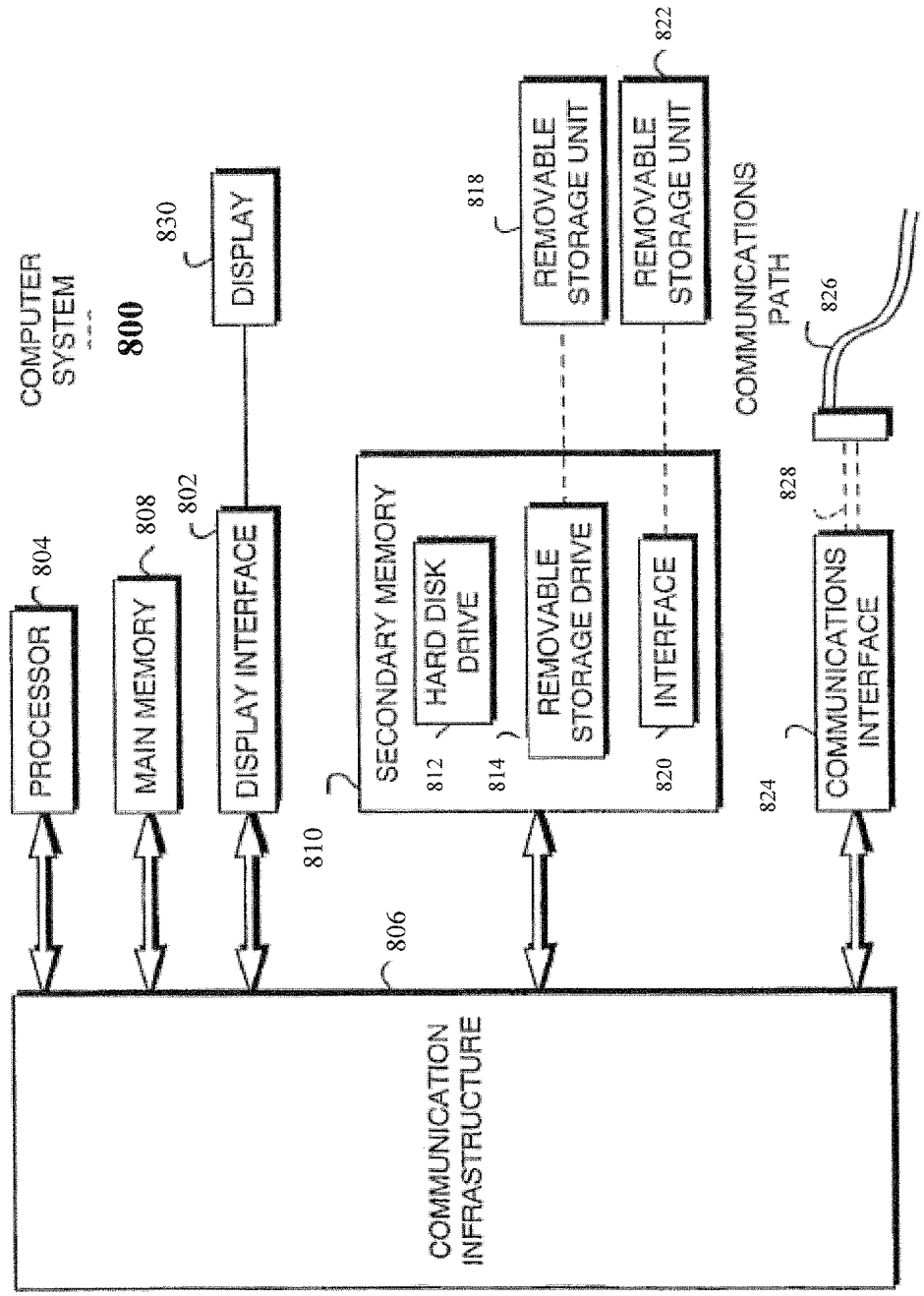
FIG. 8 is a functional block diagram for a computer system for implementation of an exemplary embodiment or portion of an embodiment of present invention.

Turning to FIG. 8, FIG. 8 is a functional block diagram for a computer system 800 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 800 as illustrated in FIG. 8. The computer system 800 may includes one or more processors, such as processor 804. The Processor 804 is connected to a communication infrastructure 806 (e.g., a communications bus, cross-over bar, or network). The computer system 800 may include a display interface 802 that forwards graphics, text, and/or other data from the communication infrastructure 806 (or from a frame buffer not shown) for display on the display unit 830. Display unit 830 may be digital and/or analog.

The computer system 800 may also include a main memory 808, preferably random access memory (RAM), and may also include a secondary memory 810. The secondary memory 810 may include, for example, a hard disk drive 812 and/or a removable storage drive 814, representing a floppy disk drive, a magnetic tape drive, an optical disk drive, a flash memory, etc. The removable storage drive 814 reads from and/or writes to a removable storage unit 818 in a well known manner. Removable storage unit 818, represents a floppy disk, magnetic tape, optical disk, etc. which is read by and written to by removable storage drive 814. As will be appreciated, the removable storage unit 818 includes a computer usable storage medium having stored therein computer software and/or data.

In alternative embodiments, secondary memory 810 may include other means for allowing computer programs or other instructions to be loaded into computer system 800. Such means may include, for example, a removable storage unit 822 and an interface 820. Examples of such removable storage units/interfaces include a program cartridge and cartridge interface (such as that found in video game devices), a removable memory chip (such as a ROM, PROM, EPROM or EEPROM) and associated socket, and other removable storage units 822 and interfaces 820 which allow software and data to be transferred from the removable storage unit 822 to computer system 800.

The computer system 800 may also include a communications interface 824. Communications interface 824 allows software and data to be transferred between computer system 800 and external devices. Examples of communications interface 824 may include a modem, a network interface (such as an Ethernet card), a communications port (e.g., serial or parallel, etc.), a PCMCIA slot and card, a modem, etc. Software and data transferred via communications interface 824 are in the form of signals 828 which may be electronic, electromagnetic, optical or other signals capable of being received by communications interface 824. Signals 828 are provided to communications interface 824 via a communications path (i.e., channel) 826. Channel 826 (or any other communication means or channel disclosed herein) carries signals 828 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 814, a hard disk installed in hard disk drive 812, and signals 828. These computer program products ("computer program medium" and "computer usable medium") are means for providing software to computer system 800. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 808 and/or secondary memory 810. Computer programs may also be received via communications interface 824. Such computer programs, when executed, enable computer system 800 to perform the features of the present invention as discussed herein. In particular, the computer programs, when executed, enable processor 804 to perform the functions of the present invention. Accordingly, such computer programs represent controllers of computer system 800.

In an embodiment where the invention is implemented using software, the software may be stored in a computer program product and loaded into computer system 800 using removable storage drive 814, hard drive 812 or communications interface 824. The control logic (software or computer program logic), when executed by the processor 804, causes the processor 804 to perform the functions of the invention as described herein.

In another embodiment, the invention is implemented primarily in hardware using, for example, hardware components such as application specific integrated circuits (ASICs).

Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

It should be appreciated that various aspects of embodiments of the present method, system, devices and computer program product may be implemented with the following methods, systems, devices and computer program products disclosed in the following U.S.

Patent Applications, U.S. Patents, and PCT International Patent Applications that are hereby incorporated by reference herein and co-owned with the assignee:

PCT/US2007/085588 not yet published filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes."

U.S. Ser. No. 11/943,226, filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes"

PCT International Application Serial No. PCT/US2005/013792, filed Apr. 21, 2005, entitled "Method, System, and Computer Program Product for Evaluation of the Accuracy of Blood Glucose Monitoring Sensors/Devices,"

U.S. patent application Ser. No. 11/578,831, filed Oct. 18, 2006 entitled "Method, System and Computer Program Product for Evaluating the Accuracy of Blood Glucose Monitoring Sensors/Devices;"

PCT International Application Serial No. PCT/US01/09884, filed Mar. 29, 2001, entitled "Method, System, and Computer Program Product for Evaluation of Glycemic Control in Diabetes Self-Monitoring Data;"

U.S. Pat. No. 7,025,425 B2 issued Apr. 11, 2006, entitled "Method, System, and Computer Program Product for the Evaluation of Glycemic Control in Diabetes from Self-Monitoring Data;"

U.S. patent application Ser. No. 11/305,946 filed Dec. 19, 2005 entitled "Method, System, and Computer Program Product for the Evaluation of Glycemic Control in Diabetes from Self-Monitoring Data" (Publication No. 20060094947);

PCT International Application Serial No. PCT/US2003/025053, filed Aug. 8, 2003, entitled "Method, System, and Computer Program Product for the Processing of Self-Monitoring Blood Glucose (SMBG) Data to Enhance Diabetic Self-Management;"

U.S. patent application Ser. No. 10/524,094 filed Feb. 9, 2005 entitled "Managing and Processing Self-Monitoring Blood Glucose" (Publication No. 2005214892);

PCT International Application Serial No PCT/US2006/033724, filed Aug. 29, 2006, entitled "Method for Improvising Accuracy of Continuous Glucose Sensors and a Continuous Glucose Sensor Using the Same;"

PCT International Application No. PCT/US2007/000370, filed Jan. 5, 2007, entitled "Method, System and Computer Program Product for Evaluation of Blood Glucose Variability in Diabetes from Self-Monitoring Data;"

U.S. patent application Ser. No. 11/925,689, filed Oct. 26, 2007, entitled "For Method, System and Computer Program Product for Real-Time Detection of Sensitivity Decline in Analyte Sensors;"

PCT International Application No. PCT/US00/22886, filed Aug. 21, 2000, entitled "Method and Apparatus for Predicting the Risk of Hypoglycemia;"

U.S. Pat. No. 6,923,763 B1, issued Aug. 2, 2005, entitled "Method and Apparatus for Predicting the Risk of Hypoglycemia;" and PCT International Patent Application No. PCT/US2007/082744, filed Oct. 26, 2007, entitled "For Method, System and Computer Program Product for Real-Time Detection of Sensitivity Decline in Analyte Sensors."

U.S. Patent Application Publication No. US2007/0287144, Dec. 13, 2007, "Biological Response Prediction System, Method for Predicting Biological Response and Computer Program Product", Kouchi,Y., et al.

U.S. Patent Application Publication No. US2007/0179771, Aug. 2, 2007, "Medical Simulation System, Computer System and Computer Program Product", Kouchi, Y., et al.

U.S. Patent Application Publication No. US2007/0118347, May 24, 2007, "Medical Simulation System and Computer Program Product, Kouchi, Y., et al.

U.S. Patent Application Publication No. US2007/0071681, Mar. 29, 2007, "Apparatus and Method for Computer Modeling Type 1 Diabetes", Gadkar, K., et al.

U.S. Patent Application Publication No. US2006/0277015, Dec. 7, 2006, "Simulation System for Functions of Biological Organs and Recording Medium in which Program Therefore is Recorded", Kouchi, Y., et al.

U.S. Patent Application Publication No. US2005/0288910, Dec. 29, 2005, "Generation of Continuous Mathematical Model for Common Features of a Subject Group", Schlessinger, L., et al.

U.S. Patent Application Publication No. 2002/0026110, Feb. 28, 2002, "Methods for Improving Performance and Reliability of Biosensors", Parris, N., et al.

REFERENCES CITED

The following patents, applications and publications as listed below and throughout this document are hereby incorporated by reference in their entirety herein. Moreover, the devices, systems, compositions, and computer program products and methods of various embodiments of the present invention disclosed herein may utilize aspects disclosed in the following U.S. Patents, foreign patents, and publications.

[1] Albisser A M, Leibel B S, Ewart T G, Davidovac Z, Botz C K, Zinggg W. An artificial endocrine pancreas. *Diabetes*, 23:389-396, 1974.

[2] Clemens A H, Chang P H, Myers R W. The development of Biostator, a glucose-controlled insulin infusion system. *Horm Metab Res Supplement*, 7: 23-33, 1977.

[3] Santiago J V, Clemens A H, Clarke W L, Kipnis D M. Closed-loop and open-loop devices for blood glucose control in normal and diabetic subjects. *Diabetes*, 28: 71-84, 1979.

[4] Anderson S M, Clarke W L, Cox D J, Gonder-Frederick, L A, and Kovatchev B P. Development of a Novel Glucose Clamping Technique for Steady Hypoglycemic Descent. *Diabetes*, 53, Supplement 2: A485, 2004.

[5] Hovorka R, Chassin L J, Wilinska Me., Canonico V, Akwi J A, Orsini-Federici M et al. Closing the loop: the Adicol experience. *Diabetes Technol Ther* 6: 307-318, 2004.

[6] Hovorka R. Continuous glucose monitoring and closed-loop systems. *Diabetic Medicine*, 23:1-12, 2005.

[7] Klonoff D C: The Artificial Pancreas: How Sweet Engineering Will Solve Bitter Problems. *J Diabetes Sci Technol*, 1: 72-81, 2007.

[8] Steil G M, Rebrin K, Darwin C, Hariri F, Saad M F. Feasibility of automating insulin delivery for the treatment of type 1 diabetes. *Diabetes* 55: 3344-3350, 2006.

[9] Senate hearing: The Potential of an Artificial Pancreas: Improving Care for People with Diabetes, Sep. 27, 2006.

[10] The JDRF e-Newsletter: Emerging Technologies in Diabetes Research, September, 2006.

[11] Benhabib B. Manufacturing: Design, Production, Automation and Integration. CRC Press, 2003. ISBN 0824742737

[12] Eddy D M, Schlessinger L. Archimedes: A Trial-Validate Model of Diabetes. *Diabetes Care*, 26: 3093-3101, 2003.

[13] Eddy D M, Schlessinger L. Validation of the Archimedes Diabetes Model. *Diabetes Care*, 26: 3102-3110, 2003.

[14] Bergman R N, Ider Y Z, Bowden C R, Cobelli C. Quantitative estimation of insulin sensitivity. *Am J Physiol.* 236:E667E677, 1979.

[15] Dalla Man C, Caumo A, and Cobelli C. The oral glucose minimal model: estimation of insulin sensitivity from a meal test. *IEEE Trans Biomed Eng* 49: 419-429,2002

[16] Dalla Man C, Caumo A, Basu R, Rizza R, Toffolo G, and Cobelli C. Minimal model estimation of glucose absorption and insulin sensitivity from oral test: validation with a tracer method. *Am J Physiol Endocrinol Metab* 287: E637 E643, 2004

[17] Dalla Man C, Yarasheski K E, Caumo A, Robertson H, Toffolo G, Polonsky K S, Cobelli C. Insulin sensitivity by oral glucose minimal models: validation against clamp. *Am J Physiol Endocrinol Metab.* 289: E954-9, 2005

[18] Basu R., Di Camillo B., Toffolo G., Basu A., Shah P., Vella A., Rizza R., Cobelli C., Use of a novel triple tracer approach to asses postprandial glucose metabolism. *Am J Physiol Endocrinol Metab.* 284: E55-69, 2003.

[19] Basu R., Dalla Man C., Campioni M., Basu A., Klee G., Jenkins G., Toffolo G., Cobelli C., Rizza R. A., Mechanisms of postprandial hyperglycemia in elderly men and women: gender specific differences in insulin secretion and action. *Diabetes* 55:2001-2014, 2006.

[20] Kovatchev B P, Gonder-Frederick L A, Cox D J, Clarke W L. Evaluating the Accuracy of Continuous Glucose Monitoring Sensors: Continuous Glucose Error-Grid Analysis (CG-EGA) Illustrated by Therasense Freestyle Navigator™Data. *Diabetes Care*, 27: 1922-1928, 2004.

[21] Clarke W L, Anderson S, Farhy L S, Breton M, Gonder-Frederick L A, Cox D J, and Kovatchev B P. Evaluating the Clinical Accuracy of Two Continuous Glucose Sensors Using Continuous Glucose-Error Grid Analysis (CG-EGA). *Diabetes Care*, 28:2412-2417, 2005.

[22] King C R, Anderson S M, Breton M D, Clarke W L, and Kovatchev B P. Modeling of Calibration Effectiveness and Blood-to-Interstitial Glucose Dynamics as Potential Confounders of the Accuracy of Continuous Glucose Sensors. *J Diabetes Sci Technol*, 1: 317-322, 2007.

[23] Nucci G., Cobelli C. Models of subcutaneous insulin kinetics. A critical review. Comput Methods Programs Biomed., 62:249-57 Review, 2000.

[24] Kovatchev B P, Clarke W L, Breton M, Brayman K, McCall A (2005). Quantifying Temporal Glucose Variability in Diabetes via Continuous Glucose Monitoring: Mathematical Methods and Clinical Application. *Diabetes Technology and Therapeutics*, 7: 849-862.

[25] McCall A, Cox D J, Crean J, Gloster M, and Kovatchev B P (2006). A Novel Analytical Method for Assessing Glucose Variability: Using CGMS in Type 1 Diabetes Mellitus. *Diabetes Technology and Therapeutics*, 8: 644-653.

[26] U.S. Patent Application Publication No. WO/2002/005702, Mault, et. al., "Closed Loop Glycemic Index System", Jan. 14, 2002.

[27] U.S. Patent Application Publication No. WO/2006/131288, Bousamra, et. al., "A System and Method Providing For User Intervention in a Diabetes Control Arrangement", Dec. 14, 2006.

[28] U.S. Patent Application 2006/0224109, Steil, et. al., "Closed Loop System For Controlling Insulin Infusion", Oct. 5, 2006.

[29] U.S. Pat. No. 7,016,720 B2, Kroll, et. al., "System and Method For Monitoring Blood Glucose Levels Using an Implantable Medical Device", Mar. 21, 2006.

[30] U.S. Pat. No. 6,923,763 B1, Kovatchev, et. al., "Method and Apparatus For Predicting the Risk of Hypoglycemia", Aug. 2, 2005.

[31] U.S. Pat. No. 6,804,551 B2, Griffin, et. al., "Method and Apparatus For the Early Diagnosis of Subacute, Potentially Catastrophic Illness", Oct. 12, 2004.

[32] R. Srinivasan, A. H. Kadish, R. Sridhar. A mathematical model for the control mechanism of free fatty acid-glucose metabolism in normal humans. Comput Biomed. Res, 3: 146-166, 1970.

[33] R. O. Foster, J. S. Soeldner, M. H. Tan, J. R. Guyton. Short term glucose homeostasis in man: a system dynamic model. Trans ASME: 308-314, 1973.

[34] C. Cobelli, G. Federspil, G. Pacini, A. Salvan, C. Scandellari An integrated mathematical model of the dynamics of blood glucose and its hormonal control. Math. Biosci, 58:27-60, 1982.

[35] C. Cobelli, A. Mari Validation of mathematical models of complex endocrine-metabolic systems: a case study on a model of glucose regulation. Med. Biol. Eng. Comput, 21: 390-399, 1983.

[36] C. Cobelli, A. Ruggeri Evaluation of portal/peripheral route and of algorithms for insulin delivery in the closed-loop control of glucose in diabetes. A modeling study. IEEE Trans. Biomed. Eng, 30: 93-103, 1983.

[37] E. Salzsieder, G. Albrecht, U. Fischer, E. J. Freys Kinetic modeling of the glucoregulatory system to improve insulin therapy. IEEE Trans Biomed Eng, 32: 846-55, 1985.

[38] J. T. Sorensen. A Physiologic Model of Glucose Metabolism in Man and Its Use to Design and Assess Improved Insulin Therapies for Diabetes. PhD thesis, Massachusetts Institute of Technology, Department of Chemical Engineering, 1985.

[39] E. D. Lehmann, T. Deutsch A physiological model of glucose-insulin interaction in type 1 diabetes mellitus J Biomed Eng, 14: 235-42, 1992.

[40] S. Andreassen, J. J. Benn, R. Hovorka, K. G. Olesen, E. R. Carson. A probabilistic approach to glucose prediction and insulin dose adjustment: description of metabolic model and pilot evaluation study. Comput Methods Programs Biomed, 41: 153-65, 1994.

[41] P. Vicini, A. Caumo, C. Cobelli, Glucose effectiveness and insulin sensitivity from the minimal models: consequence of undermodeling assessed by Monte Carlo simulation. IEEE Trans Biomed Eng, 46:130-7, 1999.

[42] R. Hovorka, V. Canonico, L. J. Chassin, U. Haueter, M. Massi-Benedetti, M. Orsini Federici, T. R. Pieber, H. C. Schaller, L. Schaupp, T. Vering, M. E. Wilinska. Nonlinear model predictive control of glucose concentration in subjects with type 1 diabetes. Physiol Meas., 25: 905-20, 2004.

[43] C. Dalla Man, R. A. Rizza, C. Cobelli. Meal Simulation Model of The Glcuose-Insulin System IEEE Trans Biomed Eng, in press 2007.

[44] R. Basu, B. Di Camillo, G. Toffolo, A. Basu, P. Shah, A. Vella, R. Rizza, C. Cobelli. Use of a novel triple tracer approach to asses postprandial glucose metabolism. Am J Physiol Endocrinol Metab., 284: E55-69, 2003.

[45] R. Basu, C. Dalla Man, M. Campioni, A. Basu, G. Klee, G. Jenkins, G. Toffolo, C. Cobelli, R. A. Rizza. Mechanisms of postprandial hyperglycemia in elderly men and women: gender specific differences in insulin secretion and action. Diabetes, 55:2001-2014, 2006.

[46] H. Yki-Jarvinen, V. A. Koivisto. Continuous subcutaneous insulin infusion therapy decreases insulin resistance in type 1 diabetes. Journal of Clinical Endocrinology & Metabolism, 58: 659-666, 1984.

[47] I. Lager, P. Lonnroth, H. Von Schenck, U. Smith. Reversal of insulin resistance in type I diabetes after treatment with continuous subcutaneous insulin infusion. British Medical Journal Clinical Research Ed, 287: 1661-1664, 1983.

[48] A. Vella, P Shah, R Basu, A Basu, M. Camilleri, W. F. Schwenk, R. A. Rizza. Type I Diabetes Mellitus Does Not Alter Initial Splanchnic Glucose Extraction or Hepatic UDP-glucose Flux during Enteral Glucose Administration. Diabetologia 44:729-737, 2001.

[49] G. Nucci, C. Cobelli. Models of subcutaneous insulin kinetics. A critical review. Comput Methods Programs Biomed., 62:249-57 Review, 2000.

[50] M. E. Wilinska, L. J. Chassin, H. C. Schaller, L. Schaupp, T. R. Pieber, R. Hovorka. Insulin kinetics in type-I diabetes: continuous and bolus delivery of rapid acting insulin. IEEE Trans Biomed Eng., 52:3-12, 2005.

[51] G. M. Steil, K. Rebrin, C. Darwin, F. Hariri, MF. Saad. Feasibility of automating insulin delivery for the treatment of type 1 diabetes. Diabetes, 55:3344-50, 2006.

[52] B. W. Bequette. A critical assessment of algorithms and challenges in the development of a closed-loop artificial pancreas. Diabetes Technol Ther. 7: 28-47, 2005.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a U.S./foreign patent, U.S./foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. An interactive computer-implemented method for testing of monitoring and treatment strategies for diabetes in an individual patient, comprising:
   providing a computer-executable model of the human glucose-insulin metabolic system;
   providing a database of a population of simulated diabetic human subjects representative of the general diabetic population, the simulated population being derived from real patient data and collectively having a set of metabolic parameters with values encompassing a distribution of parameters observed in vivo across the population of diabetic subjects;
   receiving a user input defining a treatment strategy for said individual patient and selected simulated subjects from said database on which to run the defined treatment strategy;
   running said defined treatment strategy in a computer processor on said selected simulated subjects using said human glucose-insulin model and determining glucose levels of said selected simulated subjects during running of said treatment strategy using a simulated glucose monitoring sensor;
   evaluating effects on metabolic parameters of said selected simulated subjects by said treatment strategy based on said determined glucose levels from said simulated glucose monitoring sensor; and
   outputting said evaluated effects to said user.

2. The method of claim 1, further comprising providing a model of errors of said simulated continuous glucose monitoring sensor due to errors in calibration and blood-to-interstitial glucose delays.

3. The method of claim 1, further comprising providing a model of subcutaneous insulin delivery via insulin pump.

4. The method of claim 1, wherein said user interacts with said testing method through an interactive module to implement said testing method.

5. An interactive computer simulation system for evaluation of monitoring and treatment strategies for diabetes in an individual patient, comprising:
   a computer-executable module including a model of the human glucose-insulin metabolic system;
   a database of a population of simulated diabetic human subjects representative of the general diabetic population, the simulated population being derived from real patient data and collectively having a set of metabolic parameters with values encompassing a distribution of parameters observed in vivo across the population of diabetic subjects;
   an interactive module configured to receive user input defining a treatment strategy for said individual patient and selected simulated subjects from said database on which to run the defined treatment strategy;
   a simulated glucose monitoring sensor for determining glucose levels of said selected simulated subjects;
   a computer processor configured to run said defined treatment strategy on said selected simulated subjects using said human glucose-insulin model, to determine glucose levels of said selected simulated subjects during running of said treatment strategy using said simulated glucose monitoring sensor, to determine the effects on metabolic parameters of said selected simulated subjects by said treatment strategy, and to output said evaluated effects to said user.

6. The system of claim 5, wherein said said simulated glucose monitoring sensor includes a representation of errors of a continuous glucose monitoring sensor due to errors in calibration and blood-to-interstitial glucose delays.

7. The system of claim 5, wherein said computer simulation system further comprises:
   a computer module simulating an insulin pump, said simulated insulin pump including a representation of subcutaneous insulin delivery via an insulin pump.

8. The system of claim 5,
   wherein said interactive module further allows a user to interact with said computer simulation system for implementing said testing.

9. The system of claim 5, whereby the interactive module allows a user to interact with the simulated subjects at intervals of about every 10 minutes.

10. The system of claim 5, wherein the interactive module is run by executing software that allows a user to:
    a) input a testing scenario,
    b) select simulated subjects for running the scenario, and
    c) select a set of outcome metrics to evaluate the scenario.

11. The system of claim 10, wherein the software allows a user to select a set of glucose control outcome metrics representing or indicating average glycemia, temporal glucose variability, and associated risks for hypoglycemia and hyperglycemia.

12. The system of claim 5, wherein the user input includes a schedule of meals with corresponding carbohydrate amounts.

13. The system of claim 5, wherein the interactive module allows a user to evaluate the effect of a pre-clinical treatment method on selected simulated subjects as a substitute for testing of the treatment method in live animals.

14. The system of claim 5, wherein the interactive module allows a user to evaluate the effect of a treatment method associated with a clinical protocol on selected simulated subjects.

15. The system of claim 5, further comprising a simulated insulin delivery device for delivering a continuous or scheduled dosing of a discrete amount of insulin to the simulated subjects.

16. The system of claim 15, wherein the simulated delivery device is a subcutaneous insulin pump.

17. The system of claim 5, wherein the simulated population comprises about 300 simulated subjects.

18. The system of claim 5, wherein the simulated population comprises about 200 simulated subjects.

19. The system of claim 5, wherein the simulated population comprises about 100 simulated subjects.

20. An interactive computer simulation system for evaluation of monitoring and treatment methods for diabetes in an individual patient, comprising:
    a processor configured to apply a model of the human metabolic system and provide a population of simulated human subjects representative of the general diabetic population, the simulated population derived from real patient data and collectively having a set of metabolic parameters with values encompassing a distribution of the parameters observed in vivo across the population of diabetic subjects,
    a simulated glucose monitoring sensor for continuously determining glucose levels of the simulated subjects, and software that allows a user to:
a) input a testing scenario,
b) select simulated subjects for running the scenario, and
c) select a set of outcome metrics to evaluate the scenario.

* * * * *